(12) United States Patent
Smith et al.

(10) Patent No.: US 9,726,626 B2
(45) Date of Patent: Aug. 8, 2017

(54) QUANTUM MECHANICAL MEASUREMENT DEVICE

(71) Applicant: Geometrics, Inc., San Jose, CA (US)

(72) Inventors: Kenneth R. Smith, Fremont, CA (US); Krzysztof Kiersnowski, Orinda, CA (US)

(73) Assignee: Geometrics, Inc., San Jose, CA (US)

( * ) Notice: Subject to any disclaimer, the term of this patent is extended or adjusted under 35 U.S.C. 154(b) by 1090 days.

(21) Appl. No.: 13/773,280

(22) Filed: Feb. 21, 2013

(65) Prior Publication Data

US 2013/0214780 A1  Aug. 22, 2013

Related U.S. Application Data

(60) Provisional application No. 61/601,883, filed on Feb. 22, 2012.

(51) Int. Cl.
*G01N 24/00* (2006.01)
*G01R 33/26* (2006.01)

(52) U.S. Cl.
CPC .......... *G01N 24/006* (2013.01); *G01R 33/26* (2013.01)

(58) Field of Classification Search
CPC ....... G01R 33/032; G01R 33/26; G01N 24/00
USPC .................................. 324/300, 301, 304, 5
See application file for complete search history.

(56) References Cited

U.S. PATENT DOCUMENTS

| | | | |
|---|---|---|---|
| 3,150,313 A | 9/1964 | Hans | |
| 3,257,608 A | 6/1966 | Bell et al. | |
| 3,641,426 A | 2/1972 | Brun et al. | |
| 3,652,926 A | 3/1972 | Brun | |
| 4,587,487 A | 5/1986 | Zanzucchi | |
| 5,225,778 A | 7/1993 | Chaillout et al. | |
| 5,266,896 A | 11/1993 | Rugar et al. | |
| 5,534,776 A * | 7/1996 | Leger | G01R 33/26 324/301 |
| 6,888,780 B2 | 5/2005 | Happer et al. | |
| 6,919,770 B2 | 7/2005 | Happer et al. | |
| 7,102,451 B2 | 9/2006 | Happer et al. | |
| 7,145,333 B2 | 12/2006 | Romalis et al. | |
| 7,323,941 B1 | 1/2008 | Happer et al. | |
| 7,652,473 B2 | 1/2010 | Kawabata | |
| 7,723,985 B2 | 5/2010 | Smith | |
| 7,872,473 B2 | 1/2011 | Kitching et al. | |
| 8,054,074 B2 | 11/2011 | Ichihara et al. | |
| 8,212,556 B1 | 7/2012 | Schwindt et al. | |

(Continued)

OTHER PUBLICATIONS

Aleksandrov, E.B., et al., "A Noise-Immune Cesium Magnetometer," Instruments and Experimental Techniques, vol. 50, No. 1, pp. 91-94, 2007.

(Continued)

*Primary Examiner* — Melissa Koval
*Assistant Examiner* — Rishi Patel
(74) *Attorney, Agent, or Firm* — PatentBest; Andrew McAleavey (57) ABSTRACT

A quantum mechanical measurement device is provided. A spin ensemble is provided. A first light source provides a first light at a first wavelength, wherein the first light source is positioned to provide light into the spin ensemble. A detector is positioned to detect light from the spin ensemble. A modulator modulates absorption of the first light from the first light source by the spin ensemble at a frequency greater than a Larmor frequency of the spin ensemble.

17 Claims, 6 Drawing Sheets

(56) References Cited

U.S. PATENT DOCUMENTS

| | | |
|---|---|---|
| 8,836,327 B2 | 9/2014 | French et al. |
| 2002/0051279 A1 | 5/2002 | Minemoto et al. |
| 2008/0290867 A1 | 11/2008 | Smith |
| 2011/0025323 A1 | 2/2011 | Budker et al. |
| 2011/0031969 A1 | 2/2011 | Kitching et al. |
| 2013/0147472 A1* | 6/2013 | French ................ G01R 33/032 324/252 |

OTHER PUBLICATIONS

Alexandrov, E.B., et al., "Experimental Demonstration of the Sensitivity of an Optically Pumped Quantum Magnetometer," Technical Physics, vol. 49, No. 6, pp. 779-783, 2004.

Bell, William E. and Bloom, Arnold L., "Optical Detection of Magnetic Resonance in Alkali Metal Vapor," Physical Review, vol. 107, No. 4, Sep. 15, 1957.

Bell, William E. and Bloom, Arnold, L., "Optically Driven Spin Precession," Physical Review Letters, vol. 6, No. 6, Mar. 15, 1961.

Bick, M. et al., "SQUID Gradiometry for Magnetocardiography Using Different Noise Cancellation Techniques," IEEE Trans. on Applied Superconductivity, vol. 11, No. 1, Mar. 2001.

Budker, Dmitry and Romalis, Michael, "Optical Magnetometry," Nature Physics vol. 3, Apr. 2007.

Geometrics, Inc., "Final Report: A Miniature Wide Band Atomic Magnetometer." Department of Defense Strategic Environmental Research and Development Program (SERDP) Project MR-1512, Mar. 2011.

Geometrics, Inc., "Final Report: Development of a Micro-Fabricated Total-Field Magnetometer." Department of Defense Strategic Environmental Research and Development Program (SERDP) Project MR-1512, Mar. 2011.

Jiménez-Martínez et al., "Sensitivity Comparison of Mx and Frequency-Modulated Bell-Bloom Cs Magnetometers in a Microfabricated Cell," IEEE Trans. on Instrumentation and Measurement, vol. 59, No. 2, Feb. 2010.

Kawabata, R., et al., "Improvement of an Optically Pumped Magnetometer," Japanese Journal of Applied Physics, vol. 51, 2012.

Weis, A. and Wynands, R., "Laser-Based Precision Magnetometry in Fundamental and Applied Research," Optics and Lasers in Engineering, vol. 43, pp. 387-401, 2005 (available online Jul. 27, 2004).

International Search Report dated Jul. 25, 2013 from International Application No. PCT/US2013/027145.

Written Opinion dated Jul. 25, 2013 from International Application No. PCT/US2013/027145.

Vasilakis et al., "Precision Measurements of Spin Interactions With High Density Atomic Vapors," in a Dissertation Presented to the Faculty of Princeton University in Candidacy for the Degree of Doctor of Philosophy, Sep. 2011, Chapters 5 and 7, 58 pages.

Arnold L. Bloom, "Principles of Operation of the Rubidium Vapor Magnetometer," Applied Optics, vol. 1 No. 1, Jan. 1962, pp. 61-68.

Hovde et al., Sensitive optical atomic magnetometer based on nonlinear magneto-optical rotation, *Proc. SPIE* 7693, Unattended Ground, Sea, and Air Sensor Technologies and Applications XII, 769313 May 7, 2010, 10 pages.

Higbie et al., "Robust, high-speed, all-optical atomic magnetometer," Review of Scientific Instruments, vol. 77, 113106, 2006, 8 pages.

Belfi, J. et al., "Dual Channel Self-Oscillating Optical Magnetometer," J. Optical Society of America B, vol. 26, No. 5, May 1, 2009.

Kimball, D., et al., "Magnetometric Sensitivity Optimization for Nonlinear Optical Rotation with Frequency-Modulated Light: Rubidium D2 Line," J. Applied Physics, vol. 106, No. 6, Sep. 24, 2009.

Pustelny, S., et al., "Pump-Probe Nonlinear Magneto-Optical Rotation with Frequency Modulated Light," ARXIV. ORG, Cornell University Library, Nov. 14, 2005.

* cited by examiner

QUANTUM MECHANICAL MEASUREMENT DEVICE

CROSS REFERENCE TO RELATED APPLICATIONS

This application claims priority under 35 U.S.C. §119(e) from U.S. Provisional Application No. 61/601,883, entitled "LASER-BASED ATOMIC MAGNETOMETERS", filed Feb. 22, 2012, and naming Smith et al. as inventors, which is incorporated by reference in its entirety for all purposes.

BACKGROUND OF THE INVENTION

Field of the Invention

The present invention relates to the field of magnetometers. More specifically, the present invention relates to magnetometers based on spin ensembles, for example, alkali vapor cells.

Description of the Related Art

Magnetometers are used to measure the strength and direction of a magnetic field. They can be useful in measuring minute changes in the Earth's magnetic field that allow users to identify geological conditions under the Earth's surface, such as the location of oil and mineral deposits, as well as other conditions.

A magnetometer that uses a cesium atomic vapor is described in U.S. Pat. No. 7,723,985, issued May 25, 2010 to Kenneth R. Smith, which is incorporated by reference for all purposes. The basic principle that allows cesium atomic vapor magnetometers to operate is the fact that a cesium atom can exist in several energy levels, which involve the placement of electron atomic orbitals around the atomic nucleus. When a cesium atom within the cell encounters a photon from the emitter, it jumps to a higher energy state and then re-emits a photon and falls to an indeterminate lower energy state. The cesium atom is "sensitive" to the photons from the emitter only in certain energy states. Therefore, the atoms will preferentially populate those states that do not interact with the photons. The photons therefore pass through unhindered and are measured by the photon detector. Under this condition, the cesium in the cell is optically saturated.

Once the cesium is optically saturated, the system is ready for the measurement procedure. The axis of the atomic spin precesses about the ambient magnetic field. This precession causes the alignment between the atom and the light to vary, in a cyclic manner, between an alignment that favors the absorption of light and one that reduces the absorption. If the light is pulsed on and off at the same frequency as the precession rate of the atoms, those atoms that are aligned such that they absorb the light will be driven to a higher energy state. These atoms will then decay to one of the lower energy states. When the atoms return to the lower state, the phase of their precession will have been changed. If the precession is now such that the atom is aligned so as to not absorb light when the light pulses on, the atom will remain in this state. Thus, when the light is pulsed on and off at a rate equal to the precession rate, the absorption in the cell is decreased.

The wavelength of light from the emitter is typically modulated on and off of what is called an absorption line. This is the wavelength at which the absorption of the light in the cell is maximized. In Bell-Bloom systems, the modulation may be at a frequency known as the Larmor frequency. The Larmor frequency is the frequency of the atomic spin precession and is proportional to the strength of the magnetic field. A Bell-Bloom magnetometer typically tracks the variation in the Larmor frequency, which can be used to track the strength of the magnetic field, by slightly varying the rate at which the emitter is modulated and observing the variation in absorption with the frequency of the modulation.

The absorption line, however, is not a single line but a small group of sub-lines that are wider than their spacing so as to appear as a single line. The Larmor frequency for the different sub-lines is slightly different. These different Larmor frequencies form a combined Larmor frequency depending on the populations of the various lower energy states. As the emitter is modulated off the line towards states on one side, it tends to alter the populations of those states, and consequently alter the combined Larmor frequency. As a result, the details of the modulation affect the magnetic field measurement, leading to drift and heading error.

Furthermore, a semiconductor laser emitter does not respond to the modulation immediately, because of its thermal time constants. Attempts to modulate the light output at frequencies near the Larmor frequency (at the Earth's ambient field) are phase-shifted significantly by these time delays. These phase shifts complicate the operation of the magnetometer.

SUMMARY OF THE INVENTION

To achieve the foregoing and in accordance with the purpose of the present invention, a quantum mechanical measurement device is provided. A spin ensemble with a precession resonance frequency, a precession resonance period, and an absorption resonance frequency is provided. A first light source provides a first light at a first wavelength, wherein the first light source is positioned to illuminate the spin ensemble. A detector is positioned to detect light from the spin ensemble. A modulator uses a modulating signal to change the power spectrum of the first light from the first light source at the precession resonance frequency of the spin ensemble, while maintaining an average (over certain time intervals) center frequency at or near the absorption resonance frequency.

In another manifestation of the invention, method for making quantum mechanical measurements is provided. Spins are polarized in a spin ensemble by illuminating the spin ensemble with a first light at a first wavelength, where the spin ensemble has a precession resonance frequency, a precession resonance period, and an absorption resonance frequency. The power spectrum of the first light is modulated at the precession resonance frequency of the spin ensemble, while maintaining an average center frequency at or near the absorption resonance frequency. Light from the spin ensemble is detected. The detected light is used to provide a quantum mechanical measurement of the spin polarization.

In another manifestation of the invention a magnetometer is provided. A spin ensemble is provided with a precession resonance frequency, a precession resonance period, and an absorption resonance frequency. A first light source provides a first light at a first wavelength, wherein the first light source is positioned to illuminate at least a portion of the spin ensemble. A detector is positioned to detect light from the spin ensemble. A controller receives output from the detector and determines magnetic field information from the output. A modulator modulates a power spectrum of the first light from the first light source at the precession resonance frequency of the spin ensemble, while maintaining an average center frequency at or near the absorption resonance frequency.

In another manifestation of the invention, an atomic vapor magnetometer is provided. A laser light source provides a first light at a first wavelength, wherein the first light source is positioned to illuminate at least a portion of the atomic vapor. A detector is positioned to detect light from the atomic vapor. A controller receives output from the detector and determines magnetic field information from the output. The wavelength of the laser is modulated by a current signal fed to the laser. The wavelength is a function of the internal temperature of the laser, which is affected by the current through the laser. The laser power spectrum is modulated at the precession resonance frequency of the atomic spins, while maintaining an average center frequency at or near the absorption resonance frequency. This is accomplished by a modulating signal which, in this embodiment, is the current through the laser. This modulating signal contains less than half its power (not including DC) in the frequency band between one-third the Larmor frequency and twice the Larmor frequency. For example, the modulating signal could consist of a 2 MHz carrier amplitude modulated by the Larmor precession frequency.

These and other features of the present invention will be described in more details below in the detailed description of the invention and in conjunction with the following figures.

DETAILED DESCRIPTION OF SPECIFIC EMBODIMENTS

Reference will now be made in detail to specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, specific details are set forth in order to provide a thorough understanding of the present invention. The present invention may be practiced without some or all of these specific details. In addition, well known features may not have been described in detail to avoid unnecessarily obscuring the invention.

Figure 1:
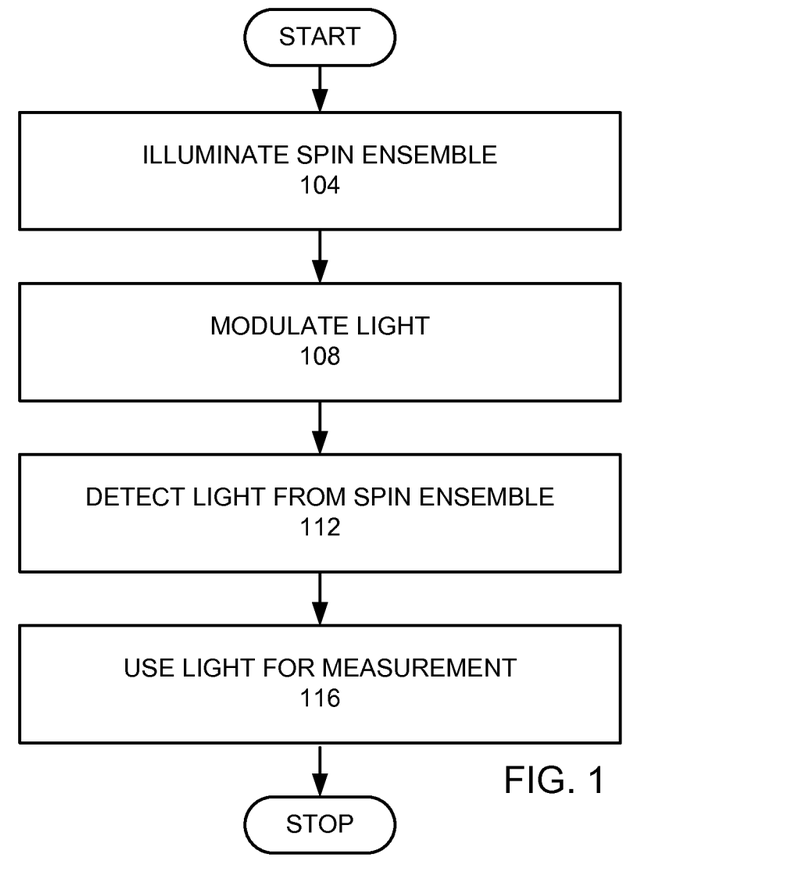
FIG. 1 is a high level flow chart of an embodiment of the invention.

FIG. 1 is a high level flow chart of an embodiment of the invention. A spin ensemble is illuminated (step 104). A spin ensemble provides at least one spin that may be modulated and probed by light. More preferably, a spin ensemble is a light addressable collection of spins. Examples of spin ensembles are atomic vapor cells, molecular vapor cells, trapped electrons, trapped protons, and nitrogen vacancy centers that allow light to interact with the spins. The illumination causes spins in the spin ensemble to be polarized. The spin ensemble has a precession resonance frequency, a precession resonance period, and an absorption resonance frequency. The power spectrum of the light is modulated (step 108) at the precession resonance frequency of the spin ensemble with a modulating signal. This modulating signal contains less than half its power (not including DC) in the frequency band between one-third the Larmor frequency and twice the Larmor frequency. The average frequency of the light may be intentionally displaced from the point of maximum absorption by some fraction of the absorption line width. "Near the absorption resonance frequency" in the specification and claims is defined as being within the full width half maximum of the absorption line. Light from the spin ensemble is detected (step 112). The detected light is used for a quantum mechanical measurement (step 116). In the specification and claims, "light" is defined as electromagnetic radiation that ranges across the spectrums of radio waves, infrared, optical, and ultraviolet radiation.

Example

Figure 2:
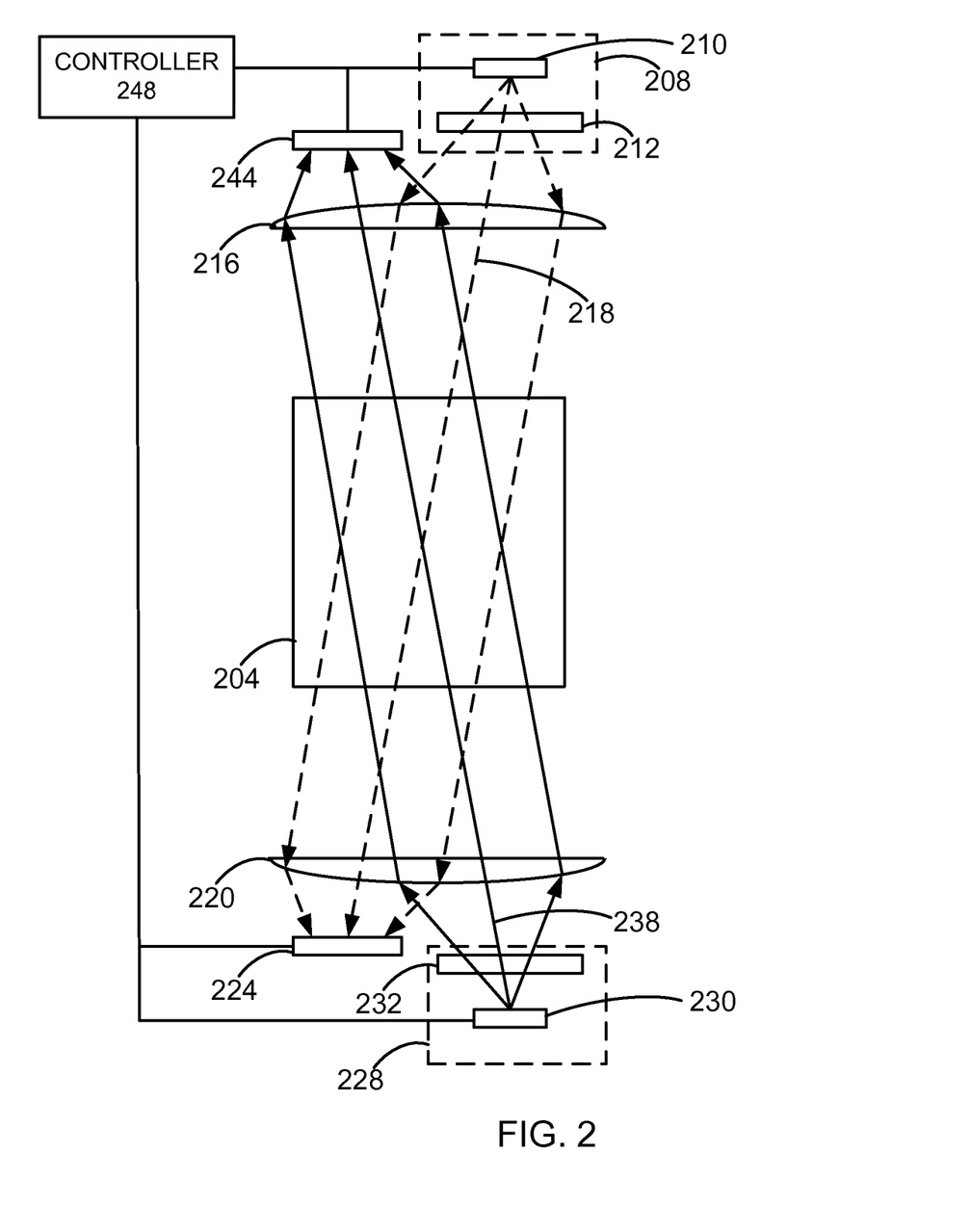
FIG. 2 is a schematic diagram of an example of an embodiment of the invention.

FIG. 2 is a schematic diagram of an example of an embodiment of the invention. In this example, a spin ensemble 204 holding a cesium atomic vapor is provided. A first light source 208 is provided, comprising a first laser diode 210 and a first polarizer 212, so that the first light source 208 provides a polarized light. A first lens 216 is placed in a first optical path 218 between the first light source 208 and the spin ensemble 204. A second lens 220 is placed on an opposite side of the spin ensemble 204 from the first lens 216 along the first optical path 218. A first detector 224 is placed on an opposite side of the second lens 220 from the spin ensemble 204 along the first optical path 218. A second light source 228 is provided, comprising a second laser diode 230 and a second polarizer 232, so that the second light source 232 provides a polarized light. The second lens 220 is placed in a second optical path 238 between the second light source 228 and the spin ensemble 204. The first lens 216 is along the second optical path 238. A second detector 244 is placed on an opposite side of the first lens 216 from the spin ensemble 204 along the second optical path 238. A controller 248 is electrically connected to the first light source 208, the second light source 228, the first detector 224, and the second detector 244. The controller 248 may also be electrically connected to other devices, such as devices that control or monitor the spin ensemble 204 or the first polarizer 212 or the second polarizer 232. In various embodiments, the controller 248 may be a single device, a plurality of devices electrically connected together, or a plurality of devices that are not electrically connected together. In addition, some components of the controller 248 may form parts of other devices, such as the first light source 208 or second light source 228.

Figure 3:
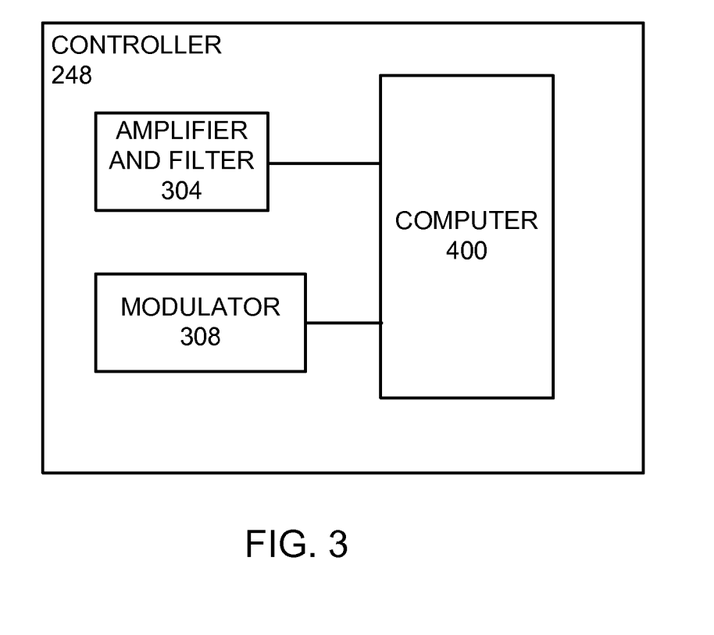
FIG. 3 is a more detailed schematic of a controller.

FIG. 3 is a more detailed schematic of the controller 248. The controller 248 comprises an amplifier and filter 304, a modulator 308, and a computer 400 electrically connected to the amplifier and filter 304 and the modulator 308. The amplifier and filter 304 is electrically connected to the first detector 224 and receives as input, output from the first detector 224. The modulator 308 is electrically connected to the first light source 208 and provides output to control the first light source 208. The amplifier and filter 304 may be a separate amplifier and separate filter or may be a single unit.

Figure 4:
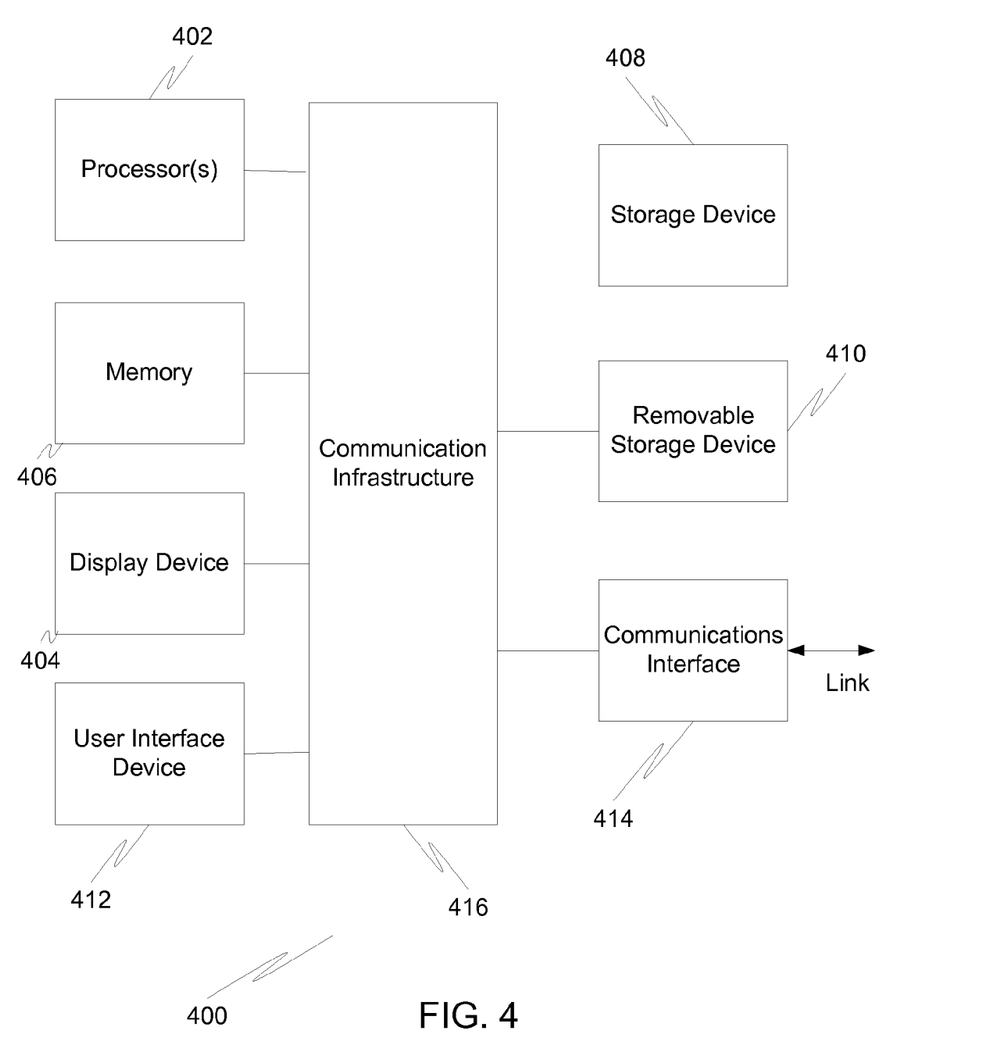
FIG. 4 is a high level block diagram showing a computer system, which may form part of the controller.

FIG. 4 is a high level block diagram showing a computer system 400, which may form part of the controller 248 in embodiments of the present invention. The computer system may have many physical forms ranging from an integrated circuit, a printed circuit board, and a small handheld device up to a huge super computer. The computer system 400 includes one or more processors 402, and further can include an electronic display device 404 (for displaying graphics, text, and other data), a main memory 406 (e.g., random access memory (RAM)), storage device 408 (e.g., hard disk drive), removable storage device 410 (e.g., optical disk drive), user interface devices 412 (e.g., keyboards, touch screens, keypads, mice or other pointing devices, etc.), and a communication interface 414 (e.g., wireless network interface). The communication interface 414 allows software and data to be transferred between the computer system 400 and external devices via a link. The system may also include a communications infrastructure 416 (e.g., a communications bus, cross-over bar, or network) to which the aforementioned devices/modules are connected.

Information transferred via communications interface 414 may be in the form of signals such as electronic, electromagnetic, optical, or other signals capable of being received by communications interface 414, via a communication link that carries signals and may be implemented using wire or cable, fiber optics, a phone line, a cellular phone link, a radio frequency link, or other communication channels. With such a communications interface, it is contemplated that the one or more processors 402 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Operation

In operation of an embodiment of the invention, the controller 248 causes the first light source 208 to provide a first polarized light along the first optical path 218 to illuminate the spin ensemble 204 (step 104). The first polarized light spin polarizes the spin ensemble. In this embodiment, the first polarizer 212 circularly polarizes the light in a counter-clockwise direction along the direction of travel of the first light. The controller 248 causes the second light source 228 to provide a second polarized light along the second optical path 238. In this embodiment, the second polarizer 232 circularly polarizes the light in a counter-clockwise direction along the direction of travel of the second light. The first light is focused by the first lens 216 and passes through the spin ensemble 204 to the second lens 220, where it is focused to the first detector 224. The second light is focused by the second lens 220 and passes through the spin ensemble 204 to the first lens 216, where it is focused to the second detector 244. The second detector 244 provides an output that is provided to the controller 248.

Figure 5:
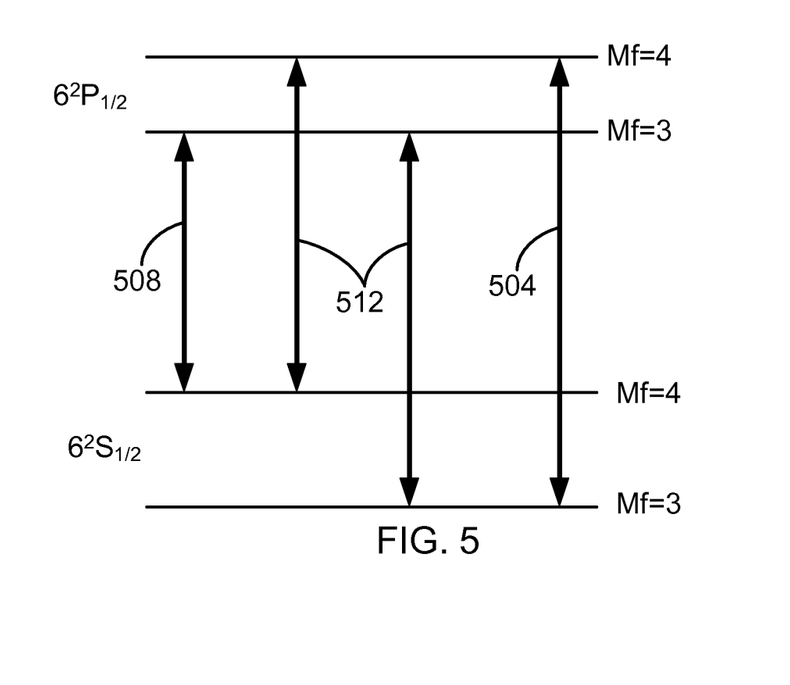
FIG. 5 illustrates the pumping and probing scheme for this embodiment of the invention.

In this embodiment, the first light and the second light are at two different frequencies. FIG. 5 illustrates the pumping and probing scheme for this embodiment of the invention. The first light, provided by the first light source 208, drives transition 508 to provide the optical pumping. The second light, provided by the second light source 228, probes the ensemble by driving transition 504. Other transitions 512 may also occur.

Figure 6:
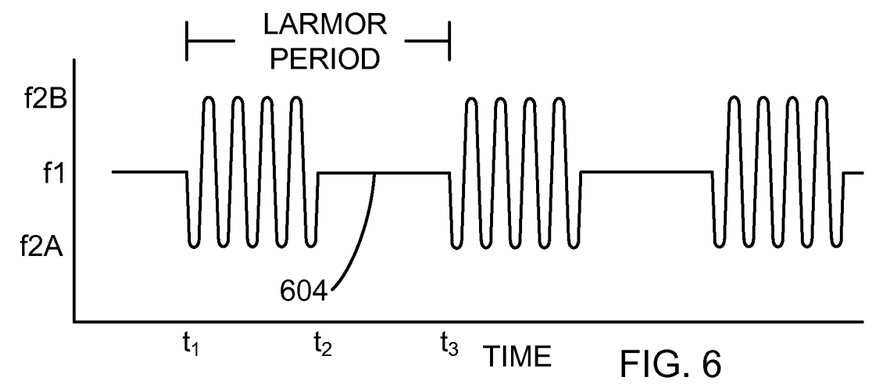
FIG. 6 is a graph of the modulated frequency of a first light from a first light source versus time, using FM modulation.

The power spectrum of the first light is modulated (step 108) at the spin precession resonance frequency of the spin ensemble with a modulating signal. FIG. 6 is a graph 604 of the effect of the modulating signal, causing a frequency modulation of the first light from the first light source 208 versus time. Considering the modulating signal as a function of time, we may calculate a Fast Fourier Transform (FFT) of this signal. A power of the FFT in a band between one-third the spin precession resonance frequency and twice the spin precession resonance frequency, is less than one-half a total power (not including DC) in the FFT. In this example, the quantum mechanical measurement is of the magnetic field. Therefore, the spin precession resonance frequency is the Larmor frequency of the spin ensemble, and the precession resonance period is the Larmor period of the spin ensemble. The modulating signal causes the following changes in the frequency of the first light. For a time prior to $t_1$, the first light is provided at frequency f1, then from $t_1$ to $t_2$ the frequency is rapidly modulated (or swept) from f2A to f2B, where f1 is near or at the center of modulation. In this example, the rapid modulation is modulated about five times. Generally, the frequency is modulated at least three times. From $t_2$ to $t_3$ the frequency is maintained at f1. This cycle is repeated at a frequency of approximately a Larmor resonance frequency for the spin ensemble 204. The period is approximately equal to the Larmor period. As a result, during part of the Larmor period the first light source is at or near the absorption resonance frequency of the vapor and for another part of the Larmor period the frequency of the first light source is rapidly modulated around the absorption resonance frequency. Therefore, this rapid modulation has a frequency greater than the Larmor frequency. Although the frequency modulation of the first light source has a square wave envelope in this example, other embodiments may provide frequency modulation with a sine wave or other envelopes. The modulation is sufficient to cause a signal that is detectable by the detector 224. In this embodiment, f2A and f2B are sufficiently spaced from f1, so that absorption at f2A and f2B is less than 90% of absorption at f1, so that at f2A and f2B there is more than a 10% reduction in absorption. The average frequency of the first light would be at or near the resonance frequency. This sweeping at a frequency more than three times faster than the precession resonance frequency forms frequency sidebands, where the average frequency is in the middle of the frequency sidebands.

Figure 7:
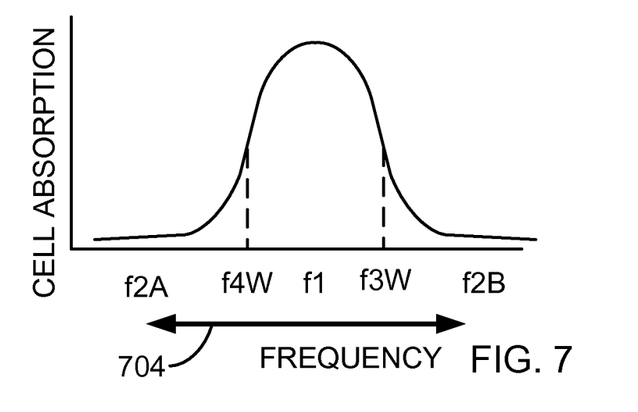
FIG. 7 is a graph of the cell absorption versus frequency.

FIG. 7 is a graph of an absorption curve of the cell absorption versus frequency. The graph is a simplified absorption curve, showing the effect of only one transition for clarity. As shown in FIG. 7, the maximum absorption is at frequency f1. The first light is FM modulated between f1 and f2A and f2B, which goes from a position of maximum absorption to positions of minimal absorptions indicated by the double headed arrow 704. In this embodiment, the modulation frequency is larger than the rate at which the cesium atoms can respond to changes in light frequency, which is about 1 MHz, and less than the frequency of the next excited state transition, which is about 1 GHz. The absorption curve has half amplitude width frequencies f3W and f4W, which are frequencies where the amplitude of absorption is half of the amplitude of absorption at the resonance frequency f1. When the average frequency is at or near the resonance frequency f1, then the average frequency is between f3W and f4W.

In this embodiment, the output from the second detector 244 is provided to the amplifier and filter 304, which acts as a bandpass filter and then provides a signal to the computer 400. The computer uses the signal to provide feedback to the modulator 308, which modulates the first light from the first light source 208.

The modulated first light interacts with the spin ensemble. The second detector 244 detects the second light 228 after passing through the spin ensemble 204 (step 112) and provides a signal to the controller 248 that signifies the amount of light detected. The detected light is used by the controller 248 to determine a quantum mechanical measurement, which in this embodiment is the strength or direction of the magnetic field (step 116). If the net polarization vector is parallel to the magnetic field, no precession signal will be measured. If the moment is moved away from the magnetic field, a measurable precession will result. By applying the modulation at the Larmor frequency, the magnetic moment is tilted away from the magnetic field, so that a precession signal can be measured. As the atoms precess in the magnetic field, they will interact with the light beam, tending to absorb the light from the beam, and producing an observable lessening of the brightness at the detector. As the atoms precess at the Larmor frequency, an amplitude modulation is produced, having a characteristic frequency equal to the Larmor frequency.

The magnetometer acts as a resonant circuit, in which a large change in absorption is obtained when modulation is applied at the Larmor frequency. The system output may be used to generate a positive feedback causing a self-oscillation at the Larmor frequency. A "self-oscillating feedback circuit", as used herein and in the claims, contains no variable-frequency-generating circuit to track the precession resonant frequency. The precession resonant frequency is generated through positive feedback. One requirement for obtaining positive feedback is ensuring that the feedback is at the proper phase, and that the phase response of the electronics does not alter resonant frequency. The embodiment of the invention requires no adjustment to the phase of the feedback signal.

Since this embodiment provides optical light paths that are substantially parallel, this embodiment provides advantages over the prior art, which may require a 90 degree phase shift, which limits the performance of the magnetometer. Other devices in the prior art may experience phase lag when moving a frequency off resonance, which may further limit the performance of the magnetometer.

The use of lasers in this embodiment of the invention allows for significantly lower power consumption than discharge lamps, and allows for a modulated amplitude or frequency.

The detectors 224, 244 may be photodetectors that measure the intensity of light directed on the detectors 224, 244. In other embodiments the detector may detect the polarization of light, wavelength, frequency, or any other property or combination of properties of light.

Additional Embodiments

Figure 8:
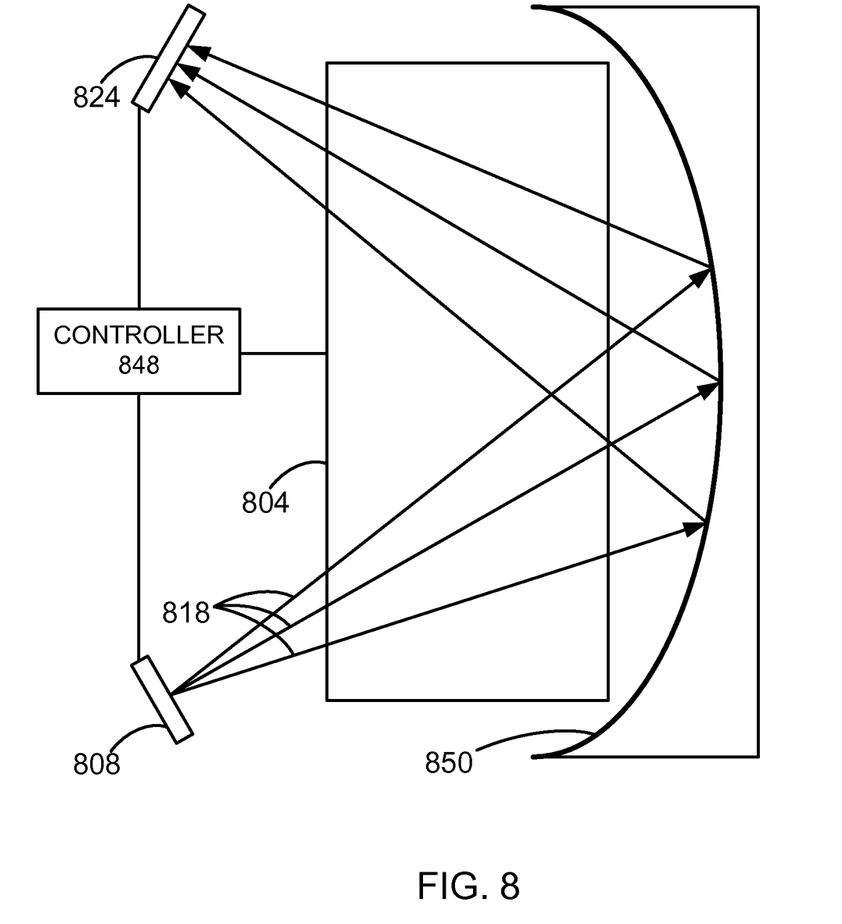
FIG. 8 is a schematic illustration of another embodiment of the invention.

FIG. 8 is a schematic illustration of another embodiment of the invention. A spin ensemble 804 contains an atomic or molecular vapor. A light source 808, a detector 824, and a focusing mirror 850 are placed adjacent to the spin ensemble 804. A controller 848 is controllably connected to the spin ensemble 804, the light source 808, and the detector 824.

In operation, the light source 808 illuminates the spin ensemble 804 by providing a polarized light along an optical path 818. After passing through the spin ensemble 804 the light is reflected by the focusing mirror 850 and passes through the spin ensemble 804 again, where the light is focused onto the detector 824. The light is detected by the detector 824, which generates a signal, which is provided to the controller 848. The controller 848 uses the detected signal to provide modulation to the light source 808 and to provide a measurement, such as a magnetic vector measurement. The controller 848 may also provide a control signal to the spin ensemble 804 to control various parameters of the spin ensemble 804, such as temperature. The controller 848 may also control other parameters of the light source 808, such as the temperature of the light source 808 or other parameters that may be used to tune the light source 808.

This embodiment is able to both pump and probe using a single laser diode. By using a single laser diode, the power requirements and number of components of this embodiment are reduced. In addition, the lenses of the previous embodiment are replaced with a focusing mirror.

Other embodiments of the invention may provide a quantum mechanical measurement device that measures gravity or time or may be used as a gyroscope or compass. In another embodiment, the polarization is in the same direction. In another embodiment, the lights are not polarized. In addition to using polarization and polarizing filters to separate pumping light from probing light, the light sources may be focused to ensure that the light is separated when reaching the detectors. In addition, an opaque screen may be used to separate the pumping light from the probe light. In addition, separation may be provided by making the optical paths orthogonal. In another embodiment, amplitude modulation may be used in place of frequency modulation. In another embodiment with two light sources, the light sources provide light of the same frequency. In some embodiments, a light source may inherently provide polarized light.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A quantum mechanical measurement device, comprising:
   a spin ensemble with a precession resonance frequency, a precession resonance period, and an absorption resonance frequency, wherein the spin ensemble is located in a closed container;
   a first light source for providing a first light at a first wavelength, wherein the first light source is positioned to illuminate and interact optically with the spin ensemble;

a detector positioned to detect light from the spin ensemble; and a modulator for modulating a power spectrum of the first light from the first light source, generating a modulating signal as a function of time;

wherein a power of the modulating signal in a frequency band between one-third the spin precession resonance frequency and twice the spin precession resonance frequency is less than one-half a total power, not including DC, of the modulating signal, and the power of the modulating signal has a peak at at least one frequency more than twice the spin precession resonance frequency.

2. The quantum mechanical measurement device, as recited in claim 1, wherein the modulator is part of a controller, which receives input from the detector and which provides a measure of a physical quantity of interest as an output.

3. The quantum mechanical measurement device, as recited in claim 2, wherein the controller computes a magnetic field from the input from the detector and
wherein the spin precession frequency is a Larmor frequency and the spin precession period is a Larmor period.

4. The quantum mechanical measurement device, as recited in claim 3, wherein the controller further comprises a processor for processing a signal from the detector to create a processed signal, which is provided to the modulator as a feedback loop.

5. The quantum mechanical measurement device, as recited in claim 4, further comprising a second light source for providing a second light, wherein the second light is directed to illuminate the spin ensemble, and wherein light from the second light source is directed to the detector and the first light is not directed to the detector.

6. The quantum mechanical measurement device, as recited in claim 5, wherein the modulator is part of a self-oscillating feedback circuit.

7. The quantum mechanical measurement device, as recited in claim 1, wherein the modulator is part of a self-oscillating feedback circuit.

8. A method for making quantum mechanical measurements, comprising:

polarizing spins in a spin ensemble by illuminating the spin ensemble with a first light at a first wavelength, wherein the spin ensemble has a precession resonance frequency, a precession resonance period, and an absorption resonance frequency, wherein the spin ensemble is located in a closed container;

modulating a power spectrum of the first light at the precession resonance frequency of the spin ensemble with a modulating signal as a function of time;

wherein a power of the modulating signal in a frequency band between one-third the spin precession resonance frequency and twice the spin precession resonance frequency is less than one-half a total power, not including DC, of the modulating signal, and the power of the modulating signal has a peak at at least one frequency more than twice the spin precession resonance frequency;

detecting light from the spin ensemble; and
using the detected light to provide a quantum mechanical measurement of the quantum state of the spin ensemble.

9. The method, as recited in claim 8, further comprising:
using the quantum mechanical measurement of the quantum state to infer a measurement of a physical quantity; and
providing an output of the measured physical quantity.

10. The method, as recited in claim 9, further comprising using a signal from the detected light to control modulation in a feedback loop.

11. The method, as recited in claim 10, further comprising using the quantum mechanical measurement of the quantum state to provide a magnetic field measurement;
wherein the spin precession frequency is a Larmor frequency and the spin precession period is a Larmor period.

12. The method, as recited in claim 10, wherein the feedback loop is used to maintain a spin polarization of the spin ensemble.

13. The method, as recited in claim 8, further comprising illuminating the spin ensemble with a second light.

14. A magnetometer, comprising:

a spin ensemble with a precession resonance frequency, a precession resonance period, and an absorption resonance frequency, wherein the spin ensemble is located in a closed container;

a first light source providing a first light at a first wavelength, wherein the first light source is positioned to illuminate at least a portion of the spin ensemble and to interact optically with the spin ensemble;

a detector positioned to detect light from the spin ensemble;

a controller for receiving output from the detector and determining magnetic field information from the output; and a modulator for modulating a power spectrum of the first light from the first light source, generating a modulating signal as a function of time;

wherein a power of the modulating signal in a frequency band between one-third the precession resonance frequency and twice the precession resonance frequency is less than one-half a total power, not including DC, of the modulating signal, and the power of the modulating signal has a peak at at least one frequency more than twice the precession resonance frequency.

15. The magnetometer, as recited in claim 14, wherein the controller processes the input from the detector to generate output to the modulator to provide a feedback loop.

16. The magnetometer, as recited in claim 15, further comprising a second light source for providing a second light, wherein the second light is directed to illuminate the spin ensemble, and
wherein light from the second light source is directed to the detector and the first light is not directed to the detector.

17. The magnetometer, as recited in claim 16, wherein the first wavelength is different than the second wavelength.

* * * * *